(12) United States Patent
Song et al.

(10) Patent No.: US 6,942,857 B2
(45) Date of Patent: Sep. 13, 2005

(54) MICROORGANISMS FOR PREVENTING AND/OR TREATING OBESITY OR DIABETES MELLITUS

(75) Inventors: Su Han Song, Chungcheongbuk-do (KR); Sun Kyung Kang, Yongin-si (KR); Jae Ho Kim, Daejeon (KR); Young Hyun Park, Daejeon (KR); Han Oh Park, Daejeon (KR)

(73) Assignee: Bioneer Corporation, Daejeon (KR)

( * ) Notice: Subject to any disclaimer, the term of this patent is extended or adjusted under 35 U.S.C. 154(b) by 0 days.

(21) Appl. No.: 10/635,858

(22) Filed: Aug. 7, 2003

(65) Prior Publication Data

US 2004/0071680 A1 Apr. 15, 2004

(30) Foreign Application Priority Data

Aug. 9, 2002 (KR) ................................ 10-2002-0047227
Jul. 21, 2003 (KR) ................................ 10-2003-0049716

(51) Int. Cl.$^7$ ............................. A23C 9/12; A23L 1/28; A01N 63/00; C12N 1/20
(52) U.S. Cl. ............................... 424/93.45; 435/252.9; 426/61
(58) Field of Search .......................... 435/252.3, 252.9; 424/439, 93.1, 93.45; 426/61

(56) References Cited

U.S. PATENT DOCUMENTS 4,568,557 A    2/1986   Becker et al.
5,234,904 A    8/1993   Swada et al.

FOREIGN PATENT DOCUMENTS

EP          0956 867 A1   11/1999

OTHER PUBLICATIONS

Robijn et al., "Structural characterization of the exopolysaccharide produced by *Lactobacillus acidophilus* LMG9433", Carbohydrate Research 288 (1996) 203–218.

Looijesteijn et al., "Regulation of Exopolysaccharide Production by *Lactococcus lactis* subsp. Cremoris by the Sugar Source", Nov. 1999, Applied and Environmental Microbiology pp. 5003–5008.

Low et al., "Role of *Streptococcus thermophilus* MR–1C Capsular Exopolysaccharide in Cheese Moisture retention", Jun. 1998, Applied and Environmental Microbiology pp. 2147–2151.

Wong et al., "Genetic organization of the cellulose synthase operon in *Acetobacter xylinum*", Oct. 1990, Proc. Natl. Acad. Sci USA vol. 87, pp 8130–8134 Genetics.

G.H. Van Geel–Schutten et al., "Biochemical and Structural Characterization of the Glucan and Fructan Exopolysaccharides Synthesized by the *Lactobacillus reuteri* Wild–type Strain and by Mutant Strains", Jul. 1999, Applied and Environmental Microbiology pp. 3008–3014.

Robijn et al., "Structural studies of the exopolysaccharide produced by *Lactobacillus paracasei* 34–1", 1996, Carbohydrate research 285 pp. 129–139.

*Primary Examiner*—David M. Naff
*Assistant Examiner*—Deborah K. Ware
(74) *Attorney, Agent, or Firm*—Nath & Associates PLLC; Gary M. Nath; Tanya E. Harkins (57) ABSTRACT

The present invention relates to microorganisms for preventing or treating obesity or diabetes mellitus which have excellent viability and produce polysaccharides efficiently in the intestines. More particularly, is directed to microorganisms for preventing or treating obesity or diabetes mellitus, which are capable of reducing the amount of monosaccharides or disaccharides that can be absorbed into the intestine by converting those mono or disaccharides into polymeric materials that cannot be absorbed in the intestines. The present invention is also directed to a pharmaceutical composition containing pharmaceutically effective amount of the microorganisms and a food composition containing the microorganisms as an active ingredient. Preferred microorganisms are *Lactobacillus reuteri* KCTC-10301BP and *Lactobacillus fermentum* KCTC-10458BP.

10 Claims, 6 Drawing Sheets

MICROORGANISMS FOR PREVENTING AND/OR TREATING OBESITY OR DIABETES MELLITUS

TECHNICAL FIELD

The present invention relates to microorganisms for preventing or treating obesity or diabetes mellitus which have excellent viability and produce polysaccharides efficiently in the intestines, more particularly, is directed to microorganisms for preventing or treating obesity or diabetes mellitus, which are capable of reducing an amount of monosaccharides or disaccharides that can be absorbed into the intestine by converting those mono or disaccharides into polymeric materials that cannot be absorbed in the intestines. The present invention is also directed to a pharmaceutical composition containing pharmaceutically effective amount of the microorganisms and a food composition containing the microorganisms as an active ingredient.

BACKGROUND ART

Obesity is well known as a chronic disease caused by various factors whose origins have not yet been clearly discovered. It is understood that obesity induces hypertension, diabetes mellitus, coronary heart disease, gall bladder disease, osteoarthritis, sleep apnea, respiratory disorder, endomerial, prostate, breast and colon cancer and the like.

According to the NIH Report (*Clinical Guideline on the Identification, Evaluation, and Treatment of Overweight and Obesity in Adults,* 1999, NIH), about 97,000,000 Americans suffer from overweight and obesity, and the number of patients of type II diabetes mellitus associated with obesity, reaches about 15,700,000. Moreover, it is also reported that about 200,000 people die of diseases associated with obesity each year (Dan Ferber, Science, 283, pp 1424, 1999).

Diabetes mellitus is one of the most widespread chronic diseases in the world, which impose a substantial expense on the public as well as on patients of diabetes mellitus and their families.

There are several types of diabetes mellitus that are caused by various etiological factors and whose pathogenesis is different from each other. For example, genuine diabetes mellitus is characterized by high level of blood glucose and glycosuria, and is a chronic disorder of carbohydrate metabolism due to a disturbance of the normal insulin mechanism.

Non-Insulin-Dependent Genuine Diabetes Mellitus (NIDDM), or the type II diabetes mellitus is found in adults who have insulin-resistance in a peripheral target tissue, despite of normal generation and function of insulin.

Non-Insulin-Dependent Genuine Diabetes Mellitus (NIDDM) is caused by three major metabolic disorders, i.e., insulin-resistance, functional disorder of insulin secretion stimulated by nutrients, and overproduction of glucose in liver. Failure to treat NIDDM, resulting in losing control of blood glucose levels, leads to death of patients from diseases such as cardiovascular disease, and/or may cause late complications of diabetes, such as retinopathy, nephropathy or neuropathy.

Accompanying diet-exercise therapy, NIDDM therapy uses sulfonylurea and biguanidine compounds to control blood glucose levels. Recently, therapeutic compounds such as metformin or acarbose have been used for treating NIDDM. However, diet-exercise therapy alone or even combined with chemotherapy using such compounds fails to control hyperglycemia in some of the diabetes mellitus patients. In such cases, these patients require exogenous insulin.

Administration of insulin is very expensive and painful to patients, and furthermore, may cause various detrimental results and various complications in patients. For example, incidences, such as, miscalculating insulin dosage, going without a meal or irregular exercise, may cause insulin response (hypoglycemia) and sometimes the insulin response occurs even without any particular reasons. Insulin injection may also cause an allergy or immunological resistance to insulin.

There are several methods for preventing or treating obesity or diabetes mellitus, including diet-exercise therapy, surgical operation and chemotherapy.

Diet-exercise therapy involves a low-calorie and low-fat diet accompanying aerobic exercise, but this therapy requiring a regular performance is hard to continue until achieving the goal.

Despite of instant effects, a surgery for physically removing body fat has limitations due to the risk and cost involved in a surgical operation and insufficient durability of the effects.

As one of the most promising therapies currently developed, pharmacotherapy can reduce blood glucose level, inhibit absorption of glucose, strengthen the action of insulin or induce the decrease of appetite. The medicines that have been developed so far use various physiological mechanisms for the prevention and the treatment of obesity and diabetes mellitus.

Among said various medicines, dietary fibers are the most useful medicine for prevention or treatment of obesity because no damage to the human metabolism-balance and use natural substances.

Microorganism dietary fiber is produced using microorganisms, such as, *Gluconobacter* sp., *Agrobacterium* sp., *Acetobacter xylinum, A. hansenii, A. pasteurianus, A. aceti, Rhizobium* sp., *Alcaligenes* sp., *Sarcina* sp., *Streptococcus thermophilus, Lactococcus cremoris, Lactobacillus helveticus, Lactobacillus bulgaricus, Lactobacillus sake, Lactobacillus reuteri, Lactobacillus lactis, Lactobacillus delbrueckii* subsp., *Lactobacillus helveticusglucose* var. *jugurti, Leuconostoc dextranicum, Bulgariscus* sp., *Campestris* sp., *Sphingomonas* sp.

Dietary fiber produced by these microorganisms is used as stabilizer, thickening agent, emulsifier, hygroscopic agent of various foods and raw materials of cosmetics and pharmaceuticals. Microorganism cellulose, xanthan, acetan, guar gum, locust bean gum, carrageenan, alginate, and agar obtained from seaweed are commercialized.

*Lactobacillus* sp. strain is the major component of normal microbial flora in the human intestines. Its significant roles for maintaining digestive organ and for healthy environment of the vagina, have been well known. [Bible, D. J., ASM News, 54:661–665, 1988; Reid G. and A. W. Bruce, In H Lappin-Scott (de.), Bacterial biofilms, Cambridge University Press, Cambridge, England, p. 274–281, 1995; Reid G., A. W. Bruce, J. A. McGroarty, K. J. Cheng, and J. W. Costerton, clin. Microbiol. Rev., 3:335–344, 1990]. Generally, *Lactobacillus* strain inhabits in digestive organs (*L. acidophilus, L. intestinalis, L. johnsonii, L. reuteri* et al.,), muscosa of the vagina (*L. vanginals, L. gasseri*), food (wine-*L. hilgardii*), *lactobacillus* beverage (*L. kefir, L. kefiranofaciens*), cheese (*L. casei*), vinegar (*L. acetotolerance*), the oral cavity (*L. oris*), yeast (*L. sake, L.* homohiochi), fruit juice (*L. kunkeei, L. mali, L. suebicus*), fermented sausages or fish (*L. farciminis, L. alimentarious*) et al.

Many people take health complementary food containing a *Lactobacillus* sp. strain in order to maintain healthy intestines and to prevent urogenital tract infection. Recently, in addition to the prevention of the diarrhea, constipation and urogenital tract infection, various probiotic activities of *Lactobacillus*, such as, control of immunity, control of cholesterol level in blood, prevention of cancer, treatment of rheumatism, alleviation of sensitivity on lactose or effect for atopic dermatitis, have been reported and thus, have attracted more attention.

According to the U.S. Public Health Service Guideline, all of the 262 *Lactobacillus* deposited in ATCC are classified as "Bio-safety Level 1," which stands for no potential risk, which has been known up to now, causing diseases in human or animals. There is no harm to human body among approximately 60 strains of *Lactobacillus*.

Recently, there has been a rapid progress in the research for an extracellular polysaccharides produced by *Lactobacillus*. It has been reported that a process of producing dietary fiber in these strains are very complicated because a lot of genes are mediated in the process, and the amount of dietary fiber thus produced are very low (Int. J. Food Microbiol., March 3 40:1–2, 87–92, 1998; Current Opinion in Microbiology, 2:598–603, 1999; Appl. Environ. Microbiol., February 64:2, 659–64, 1998; FEMS Microbiol. Rev. April 23:2 153–77, 1999; FEMS Microbiol. Rev. September 7:1–2, 113–30, 1990).

As mentioned above, although there have been various researches and efforts to develop drugs for treatment or prevention of obesity and diabetes mellitus, their results were not satisfactory. Various chemical substances mentioned above, have been developed for treatment of obesity and diabetes mellitus, but still suffer from various side effects. These drugs forcibly discharge body fat together with valuable proteins. Consequently, any one single drug for treatment or prevention of obesity and diabetes mellitus at the origin thereof does not exist yet.

Therefore, the object of the present invention is to provide microorganisms capable of living within the intestines and converting oligosaccharides produced by the digestive enzymes into non-digestible polysaccharides, and thereby remarkably reducing the amount of oligosaccharide absorbed into the intestines.

Another object of the present invention is to provide a pharmaceutical composition comprising at least one of said microorganisms in an amount effective to prevent or treat obesity and diabetes mellitus and a pharmaceutically acceptable carrier.

Another object of the present invention is to provide a food composition containing the microorganisms as an active ingredient.

DISCLOSURE OF INVENTION

The object of the present invention is achieved by providing microorganisms capable of living within the intestines and converting oligosaccharides produced by the digestive enzymes into non-digestible polysaccharides, and thereby remarkably reducing the amount of oligosaccharide absorbed into the intestines.

The microorganisms of the present invention are capable of living in the intestine and not harmful to human body, and are capable of converting oligosaccharides into polysaccharides that cannot be absorbed into human body, which are preferably *L. reuteri* PRD202, *L. fermentum* NM316.

Another object of the present invention is achieved by providing a pharmaceutical composition comprising at least one of said microorganisms in an amount effective to prevent or treat obesity and diabetes mellitus and a pharmaceutically acceptable carrier.

The pharmaceutical composition of the present invention may be administered in a form of tablet, capsule, suspension or emulsion, which comprises excipients, pharmaceutically acceptable vehicles and carriers which are selected depending on administration routes. The pharmaceutical formulation of the present invention may further comprise supplemental active ingredients.

Lactose, dextrose, sucrose, sorbitol, mannitol, starch, acacia gum, calcium phosphate, alginic acid salt, treguhkense latex, gelatin, calcium silicate, finecrystalline cellulose, polyvinylpyrolidon, cellulose, water, syrup, methylcellulose, methylhydroxybenzoate and prophylhydroxybenzoate, talc, magnesium stearate or mineral oil may be used as carriers, exipients or diluents in the pharmaceutical composition of the present invention.

In addition, the pharmaceutical composition of the present invention may further comprise lubricants, moisturizer, emulsifier, suspension stabilizer, preservative, sweetener and flavor. The pharmaceutical composition of the present invention may be in a form of an enteric coating formulation produced by various methods, which have been publicly known, in order to deliver the active ingredients of the pharmaceutical composition, i.e., microorganisms, to the small intestines without degradation by gastric juices in stomach.

Furthermore, microorganisms of the present invention may be administered in a form of capsule prepared by conventional process. For example, standard vehicles and lyophilized microorganisms of the present invention are mixed together and prepared to pellets and then, the pellets are filled into hard gelatin capsules. In addition, the microorganisms of the present invention and pharmaceutically allowable vehicles, for example, aqueous gum, cellulose, silicate or oil are mixed to produce a suspension or emulsion and then, this suspension or emulsion may be filled into soft gelatin capsule.

The pharmaceutical composition of the present invention may be prepared as an enterically coated tablets or capsules for oral administration. The term "the enteric coating" of this application includes all conventional pharmaceutically acceptable coating that has resistance to gastric juice, however, in the small intestines, can disintegrate sufficiently for a rapid release of the microorganisms of the present invention.

The enteric coating of the present invention can be maintained for more than 2 hours in synthetic gastric juice, such as HCl solution of pH 1 at the temperature of 36° C. to 38° C. and desirably, decomposes within 0.5 hours in synthetic intestinal juice, such as $KH_2PO_4$ buffer solution of pH 6.8.

The enteric coating of the present invention applies to each tablet with the amount of about 16 to 30 mg, desirably 16 to 25 mg, more desirably 16 to 20 mg. The thickness of enteric coating of the present invention is 5 to 100 $\mu$m, desirably 20 to 80 $\mu$m. The components of the enteric coating are selected appropriately from common polymeric materials, which have been publicly well known.

The polymeric materials which may be employed for enteric coating of the present invention are enumerated and described in the flowing articles [The Theory and Practice of Industrial Pharmacy, 3rd Edition, 1986, pp. 365–373 by L. Lachman, Pharmazeutische Technologie, thieme, 1991, pp. 355–359 by H. Sucker, Hagers Handbuch der Pharmazeutischen Praxis, 4th Edition, Vol. 7, pp. 739–742 and 766–778, (SpringerVerlag, 1971), and Remington's Pharmaceutical Sciences, 13th Edition, pp. 1689–1691 (Mack Publ., Co., 1970)]. For example, cellulose ester derivative, cellulose ether and copolymer of acryl and methyl acrylate or maleic acid or phthalic acid derivative may be used in enteric coating of the present invention.

The preferred enteric coating of the present invention is prepared from polymers of cellulose acetate phthals or trimelitate and methacrylic copolymer (for example, copolymer of more than 40% of methacrylic acid and methacrylic acid which contains hydroxyprophyl methylcellulose phthalate or derivatives from ester thereof). Eudragit L 100-55 manufactured by Rohm GmbH of Germany may be used as a raw material for the enteric coating of the present invention.

Cellulose acetate phthalate employed in the enteric coating of the present invention, has about 45 to 90 cP of viscosity, 17 to 26% of acetyl contents and 30 to 40% of phthalate contents. The cellulose acetate trimelitate used in the enteric coating, has about 15 to 20 cP of viscosity, 17 to 26% of acetyl contents, and 25 to 35% of trimelityl contents. The cellulose acetate trimelitate which is manufactured by the Eastman Kodak Company may be used as a material for the enteric coating of the present invention.

Hydroxyprophyl methylcellulose phthalate used in the enteric coating of the present invention has molecular weight of 130,000 dalton, desirably 80,000 to 130,000 dalton and has 5 to 10% of hydroxyprophyl contents, 18 to 24% of methoxy contents, and 21 to 35% of phthalyl contents. Cellulose acetate phthalate manufactured by the Eastman Kodak Company can be used as a material for the enteric coating of the present invention.

Hydroxyprophyl methylcellulose phthalate used in the enteric coating of the present invention is HP50 which is manufactured by the Shin-Etsu Chemical Co. Ltd., Japan. The HP50 has 6 to 10% of hydroxyprophyl contents, 20 to 24% of methoxy contents, 21 to 27% of phthalyl contents, and molecular weight is 84,000 dalton. Another material for enteric coating manufactured by the Shin-Etsu Chemical Co. Ltd., is HP55. HP55 can also be used as material for the enteric coating of the present invention. The HP55 has 5 to 9% of hydroxyprophyl contents, 18 to 22% of methoxy contents, 27 to 35% of phthalyl contents, and molecular weight is 78,000 dalton.

The enteric coating of the present invention is prepared by using conventional methods of spraying the enteric coating solution to the core. Solvents used in the process of the enteric coating are alcohol such as ethanol, ketone such as acetone, halogenated hydrocarbon such as dichloromethane, or the mixture thereof. Softeners such as Di-n-butylphthalate and triacetin are added to the enteric coating solution in the ratio of 1 part coating material to about 0.05 or to about 0.3 part softner.

A spraying process is preferably performed continuously, and the amount of materials sprayed may be controlled depending on the condition of the coating process. Spraying pressure may be regulated variously and, generally, desirable result can be obtained under the pressure of average 1 to 1.5 bar.

"The effective amount" of this specification means the minimum amount of the microorganisms of the present invention, which can reduce the amount of oligosaccharide absorbed into the body through the intestines of mammalian animals. The amount of microorganisms administered into a body with the pharmaceutical composition of the present invention may be adjusted depending on the administration method and the administration subject.

The composition of the present invention may be administered once or more per day on the subject. The unit of administration amount means that it is separated physically and thus is suitable for the unit administration for the human subjects and all other mammalian animals. Each unit contains a pharmaceutically acceptable carrier and the amount of the microorganisms of the present invention, which are effective in therapy.

An oral administration unit of an adult patient contains microorganisms of the present invention in an amount, desirably, 0.1 g or more, and the composition of the present invention contains 0.1 to 10 g per one time administration, desirably 0.5 to 5 g. The effective amount of microorganisms of the present invention is 0.1 g per 1 day.

However, the administration amount can vary depending on the weight and the severity of obesity of the patient, supplemental active ingredients included and microorganisms used therein. In addition, it is possible to divide up the daily administration amount and to administer continuously, if needed. Therefore, range of the administration amount does not limit the scope of the present invention in any way.

Another object of the present invention is achieved by providing a food composition containing the microorganisms as an active ingredient.

The "composition" of the present invention means not only as medicinal products but also to serve as general foods such as yogurt and jelly, functional foods and health complementary foods.

In case of taking the composition of the present invention periodically, microorganisms form colony within the intestines and interrupt absorption of oligosaccharide in the body competitively. Also, non-digestible fibers produced by microorganisms make a healthy condition for other useful microorganisms within the intestines and stimulate the intestinal activity. Consequently, the composition of the present invention functions to treat and prevent obesity and diabetes mellitus.

BRIEF DESCRIPTION OF THE DRAWINGS

The above objects and other advantages of the present invention will become more apparent by describing in detail a preferred embodiment thereof with reference to the attached drawings, in which.

BEST MODE FOR CARRYING OUT THE PRESENT INVENTION

Hereinafter, the present invention will be described more in detail.

The microorganisms which can be used in the pharmaceutical composition of the present invention for preventing and treating obesity and diabetes mellitus, or in a method therefore, should satisfy the requirements of 1) being capable of proliferating within the intestinal layers, 2) being capable of absorbing oligosaccharide rapidly and of converting them into non-digestible or hardly digestible high molecular weight materials, such as fibrous materials, and 3) being harmless to human body and animals. All microorganisms that can satisfy the above requirements can be used as active principles of the pharmaceutical composition of the present invention. The microorganism of the present invention may be obtained from the numerous microorganism depository institutions in the world or may be a novel microorganism isolated newly.

The polysaccharide-producing microorganisms of the present invention were obtained in the following two (2) ways:

First, the polysaccharide-producing known microorganisms were obtained from the numerous institutions. A mother organism for mutation was selected by measuring polysaccharide productivity, glucose consumption rate and resistance against gastric acid or bile acid of the microorganisms. The mother microorganism was mutated by a chemical compound and as a result, PRD202 was selected for its high productivity of polysaccharide.

It was ascertained that PRD202 falls within the *Lactobaccillus reuteri*. PRD202 was named as *Lactobacillus reuteri* PRD202(hereinafter, *Lactobacillus* PRD202). *Lactobacillus* PRD202 was deposited in KCTC (Korean Collection for Type Cultures) and was granted as KCTC 10301BP.

Second, the lactic acid bacteria were obtained from feces. A mother organism for mutation was selected by measuring polysaccharide productivity, glucose consumption rate and resistance against gastric acid or bile acid of the microorganisms. The mother microorganism was mutated by a chemical compound and as a result, NM316 was selected for its high productivity of polysaccharide.

It was ascertained that NM316 falls within the *Lactobacillus fermentum*. NM316 was named as *Lactobacillus fermentum* NM316 (hereinafter, *Lactobacillus* NM316). *Lactobacillus* NM316 was deposited in KCTC and was granted as KCTC 10458BP. Upon determining whether or not polysaccharides produced by *Lactobacillus* PRD202 and *Lactobacillus* NM316 were digestible with intestinal digestive enzymes, it was confirmed that such polysaccharides were neither digested with intestinal digestive enzymes nor absorbed into the body and that finally excreted out of the body.

In addition, upon measuring the activity of beta-glucuronidase produced by the microorganisms of the present invention, it was ascertained that the microorganisms has no harm caused by beta-glucuronidase because the microorganisms did not produce beta-glucuronidase at all.

The body weight of rats had been decreased approximately 6.5% and the amount of feed intake of rats had been decreased approximately 8.3%, as compared with a control group after the administration of *Lactobacillus* PRD202 of the present invention. Metabolism efficiency of *Lactobacillus* PRD202 was 5.6% higher than the control group and thus it was confirmed that the microorganism of the present invention has an effect in losing body weight.

The increase of the body weight of rats had been decreased approximately 16.1% and 6.3% as compared with the control group, which produce a small amount of polysaccharides, when *Lactobacillus* NM316 was administered respectively in the form of live organism itself and in the form of yogurt.

In addition, 40 days later, the increase of body weight of rats had been decreased 10.3% in the group where *Lactobacillus* NM316 was administered in the form of live organism itself and 60 days later, the increase of body weight of rats had been decreased 4.3% in the group where *Lactobacillus* NM316 was administered in the form of yogurt, as compared with the control group.

The amount of feed intake had been decreased approximately 10.7% in the group where *Lactobacillus* NM316 was administered in the form of live organism itself and had been increased approximately 4.6% in the group where *Lactobacillus* NM316 was administered in the form of yogurt.

Based on the above results, the increase of body weight versus the amount of feed intake was calculated for metabolism efficiency. As a result, metabolism efficiency of the group where *Lactobacillus fermentum* NM316 was administered in the form of live organism itself was about 6.4% higher than that of the control group when the metabolism efficiency was measured every other day. In addition, metabolism efficiency of the group where *Lactobacillus* NM316 was administered in the form of yogurt was about 28.5% higher than that of the control group when the metabolism efficiency was measured every 12 days. Therefore, it was confirmed that the microorganism of the present invention has an effect on decreasing the increase of body weight versus the amount of feed consumption.

In addition, upon measuring the change of blood cholesterol level, blood cholesterol level of the group taking the microorganism of the present invention was significantly lower than that of the group taking physiological saline solution.

Therefore, it was learned that the microorganism of the present invention and food composition containing the microorganism as an active principle were effective for obesity, diabetes mellitus and circulatory disease (for example, arteriosclerosis, myocardial infarction). In addition, it was learned that the microorganism of the present invention did not cause side effects such as hypoglycemia.

Hereinafter, the present invention will be further explained with reference to the following examples. The examples are given only for illustration of the invention and are not intended to limit the scope of the present invention.

EXAMPLE 1

Selecting of Microorganism Which Produces a Large Amount of Polysaccharide

In order to obtain a mother strain of *Lactobacillus* PRD202 which produces a large amount of dietary fiber, six (6) kinds of the known microorganisms were selected and then polysaccharides productivity, glucose consumption rate and resistance against gastric acid and bile acid were measured for selecting a mother strain which would be mutated.

Figure 1:
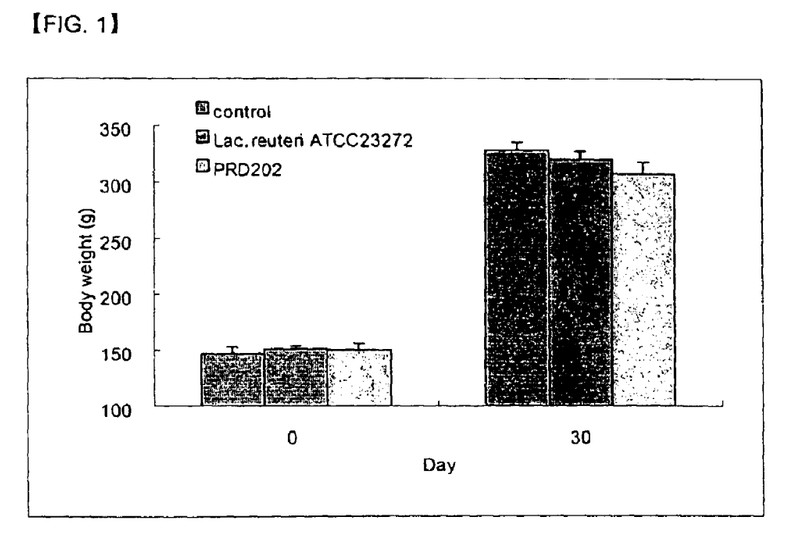
FIG. 1 is the graph illustrating the change of the body weight of rat that has taken the microorganism of the present invention in the form of live microorganism itself.

In order to measure the glucose consumption rate of each microorganism, each *Lactobacillus* strain stored at a −80° C., was inoculated into each 10 ml cap tube and was activated in the incubator for 24 hours. The activated microorganisms were inoculated in 100 ml Man Rogosa Sharp (MRS) medium (2% glucose, 1% beef extract, 1% peptone, 0.5% yeast extract, 0.1% Tween-80, 0.2% ammonium citrate, 0.5% sodium acetate, 0.01% $MgSO_4$, 0.005% $MnSO_4$, 0.05% L-cysteine HCl) and then samples were collected every 3 hours to measure the glucose consumption rate. As illustrated in FIG. 1, *Lactobacillus reuteri* ATCC 23272 showed the most excellent glucose consumption rate, 1.21 g/L/hr.

In order to measure the polysaccharide productivity of each strain, 0.5 ml of each strain cultivated in MRS medium for 24 hours was transferred to each tube and then centrifuged at 13,000 g for 20 minutes. The same amount of 40% trichloroacetate was added to the collected supernatants and then vigorously stirred. Supernatants were obtained through centrifugation at 13,000 (g) for 20 minutes and mixed with two volume of cold ethanol (4° C.) and then were stirred and centrifuged at 6,000 (g) for 10 minutes. After supernatants were carefully discarded, polysaccharides were suspended with distilled water having the same amount of the original volume and the amount of polysaccharides was measured by means of phenol-sulfuric acid method. As illustrated in Table 2, it is confirmed that polysaccharide productivities of *Lactobacillus reuteri* ATCC 23272 and *Lactobacillus reuteri* KCTC3679 were excellent.

Meanwhile, in order to measure the viability of each strain in the stomach and duodenum, $10^6$ of each strain was inoculated into pH1.5 artificial gastric juice and 2 hours later, viability of each strain was measured. As illustrated in Table 2, *Lactobacillus reuteri* ATCC 23272 showed the most excellent viability in the gastric juice. In addition, upon measuring viability of each strain in the artificial bile acid by using bile extract (Cat. B-8631 sigma, USA), *Lactobacillus reuteri* ATCC 23272 showed the most excellent viability.

From the above results, it is confirmed that *Lactobacillus reuteri* ATCC 23272 was the most excellent in terms of polysaccharide productivity, glucose consumption rate and resistance against the artificial gastric juice and bile acid. Therefore, *Lactobacillus reuteri* ATCC 23272 was selected for the mother strain which would be mutated.

TABLE 1

Comparison of growth rate and glucose consumption rate of each strain

| Name of strain | Growth rate (O.D./hr) | Glucose consumption rate (g/L/hr) | Yield (Ys/x) |
|---|---|---|---|
| Lactobacillus helveticus KCTC 3545 | 0.038 | 0.75 | 0.051 |
| Lactobacillus reutrei KCTC 3679 | 0.083 | 1.2 | 0.064 |
| Lactobacillus delbrueckii subsp. bulgaricus KCTC3635 | 0.02 | 0.67 | 0.033 |
| Lactobacillus reutrei ATCC 23272 | 0.071 | 1.21 | 0.082 |
| Lactobacillus sake ATCC 15578 | 0.054 | 1.32 | 0.041 |
| Lactobacillus rhamnosus ATCC 9595 | 0.013 | 1.1 | 0.083 |

TABLE 2

Viability in the bile acid and the artificial gastric juice and the amount of the produced exopolysaccharides (hereinafter, EPS)

| Name of strain | Viability in the artificial gastric juice(%) | Viability in the bile acid (%) | The amount of the produced EPS (mg/L) |
|---|---|---|---|
| Lactobacillus helveticus KCTC 3545 | 0.25 | 1.2 | 120 |
| Lactobacillus reutrei KCTC 3679 | 10 | 791 | 660 |
| Lactobacillus delbrueckii subsp. bulgaricus KCTC3635 | $5.3 \times 10^{-3}$ | 9.8 | 250 |
| Lactobacillus reutrei ATCC 23272 | 25.5 | 667 | 670 |
| Lactobacillus sake ATCC 15578 | 0.5 | 1.5 | 250 |
| Lactobacillus rhamnosus ATCC 9595 | 37 | 27.5 | 320 |

Viability in the artificial gastric juice (pH 1.5) was measured after 2 hour incubation.
Viability in the bile acid was measured after 9 hour incubation.
* Viability = the number of initial inoculated microorganisms(cfu/ml)/the number of microorganisms survived after incubation(cfu/ml)

Meanwhile, the mother strain of a novel microorganism NM316 used for the present invention was isolated as follows.

First, in order to find out lactic acid bacteria producing a large amount of viscous material, feces samples were collected from healthy infants who were born in Chungju, Republic of Korea and reared at the breast during 6 months. The samples were diluted tenfold with physiological saline solution and inoculated into pH1.5 MRS liquid medium and incubated at 37° C. for 5 hours. The incubated sample was spread on several MRS media and lactic acid bacteria-selection media (LBS agar) and incubated at 37° C. for 48 hours to obtain 5 to 30 colonies per plate.

Viscosity of each colony was confirmed by using a toothpick and thus the mucoid colony was selected for the strain producing mucoid. The selected strain was smeared on MRS agar medium more than two times so as to be purely isolated. Only *Lactobacillus* species were selected out from each colony by means of PCR method using the primer specific for *Lactobacillus* species.

EXAMPLE 2

Obtaining the Mutated Strain Producing a Large Amount of Polysaccharides

In order to obtain the mutated strain producing a large amount of dietary fiber, the mother strain was incubated in modified MRS medium at 37° C. for 6 hours and centrifuged to obtain the precipitation. The precipitated microorganism was rinsed once with phosphate buffered saline (PBS, pH 7.0).

After NTG (N-methyl-N-nitro-N-nitrosoguanidine) was added until the final concentration became 200 μg/ml, the microorganism was incubated at 37° C. for 30 to 120 minutes so that 99.9% of the microorganism became extinct. In order to avoid reverse-mutation of the mutated microorganism, the microorganism was transferred three times to MRS liquid medium.

The mutated microorganism thus obtained was diluted properly to form approximately 30 colonies per plate and smeared on MRS medium containing high concentration of sucrose (5% sucrose, 1% beef extract, 1% peptone, 0.5% yeast extract, 0.1% Tween-80, 0.2% Ammonium citrate, 0.5% sodium acetate, 0.01% $MgSO_4$, 0.005% $MnSO_4$, 0.05% L-cysteine HCl) to incubate at 37° C. for 48 hours.

In order to select the mutated microorganism from *Lactobacillus reuteri* ATCC 23272, viscosity of approximately 2,000 colonies which were formed on the MRS agar medium was respectively measured by using sterilized toothpicks so as to select 100 strains having viscosity. In the case of microorganism isolated from feces, 9 mutated strains were selected therefrom and inoculated into each screw-cap tube filled with 10 ml MRS and incubated without shaking at 37° C. for 24 hours.

In order to measure the polysaccharide productivity of each strain after 24 hour incubation, 0.5 ml of each strain cultivated in MRS medium for 24 hours was transferred to each tube and then centrifuged at 13, 000 g for 20 minutes. The same amount of 40% trichloroacetate was added to the collected supernatants and then vigorously stirred. Supernatants were obtained through centrifugation at 13,000 (g) for 20 minutes and mixed with two volume of cold ethanol (4° C.) and then were stirred and centrifuged at 6,000 (g) for 10 minutes. After supernatants were carefully discarded, polysaccharides were suspended with distilled water having the same amount of the initial volume and the amount of polysaccharides was measured by means of phenol-sulfuric acid method.

$$EPS \text{ yield} = \frac{EPS \text{ (mg/L)}}{O.D(650 \text{ nm})}$$

The strains having high polysaccharide yield were obtained by mutating the microorganism obtained in the above again in the same way. As a result, *Lactobacillus* PRD 202 and *Lactobacillus* NM316 were obtained respectively from *Lactobacillus reuteri* ATCC 23272 and from the microorganism isolated from feces. *Lactobacillus* PRD 202 and *Lactobacillus* NM316 showed the polysaccharide productivity respectively 4 to 5 times higher than each mother strain (Table 3).

TABLE 3

Comparison of EPS yield between the mother strain and the mutated strains

| Name of strain | O.D (650 nm) ① | EPS (mg/L) ② | EPS yield (② ÷ ①) |
|---|---|---|---|
| *Lactobacillus reuteri* ATCC 23272 | 5.15 | 673.5 | 130.8 |
| *Lactobacillus reuteri* PRD 202 | 2.10 | 1266.5 | 602.8 |
| *Lactobacillus fermentum* NM 316 | 1.41 | 714 | 506.4 |

EXAMPLE 3

Characteristics of *Lactobacillus* PRD202 and NM316 and Identification Thereof.

In order to analyze phylogenesis of PRD202 and NM316 of which EPS yield had been increased, each strain was inoculated into MRS liquid medium and incubated without shaking at 37° C. for 12 hours.

Cultured mediums were centrifuged at 6,000 rpm in 4° C. to obtain microorganisms and the nucleic acids thereof were isolated by means of using the CTAB/NaCl method. Upon determining the nucleotide sequence of 16s rRNA by using 16s rRNA consensus primer, *Lactobacillus* PRD202 was identified as *Lactobacillus reuteri* and *Lactobacillus* NM316 was identified as *Lactobacillus fermentum*.

In addition, the utilization rate of each sugar was measured in the above two microorganisms by using API 50 CH Kit (BioMerieux Co.). As a result, the utilization rates of sugars of *Lactobacillus* PRD202 were little different from those of the mother microorganism. NM316 extensively utilized L-arabinose, ribose, galactose, glucose, maltose, lactose, mellibiose and fructose, however, showed low growth rate in D-raffinose and gluconate.

Upon consideration of the result of analysis of phenotype and 16s rRNA DNA sequence, the microorganisms of the present invention were named respectively as *Lactobacillus reuteri* PRD202 and *Lactobacillus fermentum* NM316. They were deposited in KCTC (Korean Collection for Type Cultures) and the deposit number were granted as KCTC10301 BP (*Lactobacillus* PRD202) and KCTC10458BP (*Lactobacillus* NM316), respectively.

EXAMPLE 4

The Degree of Decomposition of Extracellular Polysaccharide (Dietary Fiber) by Intestinal Digestive Enzymes In order to determine whether or not dietary fiber produced by said microorganisms is decomposed by intestinal digestive enzyme, the digestive enzymes isolated from the small intestine of a rat, Porcine α-amylase (Sigma, A-3176) and Pancreatin (Sigma, P-1625) having various concentrations were added to purified polysaccharides resolved in phosphate buffered saline. After 60 minutes reaction, the amount of glucose resulted from the decomposition by the enzymes was measured by using trinder kit (cat. 315-500 Sigma, USA) by means of enzyme coloring method.

As illustrated in Table 5, it was confirmed that polysaccharides produced by *Lactobacillus reuteri* PRD202 and *Lactobacillus fermentum* NM316 were not decomposed by the intestinal digestive enzymes.

TABLE 4

The decomposition of polysaccharides caused by intestinal digestive enzymes

| | | The amount of glucose resulted from the decomposition by the enzymes (mg/dl) | | |
|---|---|---|---|---|
| Enzyme | Enzyme Conc. (ug/ml) | Starch | EPS from - *Lactobacillus reuteri* PRD202 | EPS from *Lactobacillus fermentum* - NM316 |
| RI | 500 | 197.73 | 11.20 | 5.68 |
| (Rat | 250 | 160.33 | 7.12 | 3.68 |
| intestinal | 125 | 103.30 | 5.20 | 1.52 |
| protein) | 62.5 | 56.25 | 3.20 | 0.88 |
| | 31.25 | 28.20 | 1.28 | 0.40 |
| PA | 500 | 39.11 | 3.76 | 1.36 |
| (Porcine α- | 250 | 38.02 | 2.64 | 0.64 |
| amylase) | 125 | 31.48 | 2.08 | 0.40 |
| | 62.5 | 42.38 | 1.76 | 0.32 |
| | 31.25 | 49.39 | 1.68 | 0.32 |
| PT | 500 | 61.55 | 3.04 | 1.12 |
| (Pancreatin | 250 | 48.46 | 2.48 | 1.12 |
| from | 125 | 45.96 | 1.92 | 0.48 |
| porcine) | 62.5 | 47.99 | 2.00 | 0.40 |
| | 31.25 | 52.51 | 1.76 | 0.40 |

EXAMPLE 5

Determining Whether or Not Beta-Glucuronidase was Produced by *Lactobacillus reuteri* PRD202 and *Lactobacillus fermentum* NM316

Beta-glucuronidase produced by intestinal microorganisms delays the degradation of carcinogenic aromatic compounds such as benzopyrene and interferes with the degradation of toxins produced in the body to delay the detoxification in the liver.

Therefore, in order to determine whether or not beta-glucuronidase was produced by the microorganisms of the present invention, absorbance was measured by using hydrolysis of PNPG (para-nitrophenyl-beta-D-glucuronide) (Cat. N-1627, Sigma, USA.).

At first, after each microorganism was incubated in the 300 ml MRS medium at 37° C. for 24 hours, the cultivated medium was centrifuged to recover microorganisms.

The recovered microorganisms were rinsed twice with phosphate buffered saline and suspended again in 10 ml of GUS buffer (100 mM sodium phosphate-2.5 mM EDTA (pH 6.0)). After the suspension was disrupted by using a sonicator, debris such as cell wall were eliminated through centrifugation.

50 to 400 μl of cell extract thus obtained was mixed and reacted with 500 μl of GUS buffer containing 12.5 mM of PNPG in a water bath at 37° C. for 15 minutes.

After the interruption of the reaction by using 1M $Na_2CO_3$, absorbance was measured at 405 nm ($OD_{405}$). The activity of beta-glucuronidase (1 unit) was measured by using the standard sample (Cat. G-8162, Sigma, USA) and the results thereof were illustrated in Table 6.

As a result, it was confirmed that the microorganisms of the present invention had no harm caused by beta-glucuronidase because they did not produce beta-glucuronidase at all.

TABLE 5

The activity of beta-glucuronidase

| Sample | absorbance (405 nm) | remark |
| --- | --- | --- |
| Beta-glucuronidase | 0.397 | 1 unit |
|  | 1.054 | 4.3 unit |
|  | 1.765 | 8.7 unit |
| Control strain | 0.088 | After 9 hour incubation |
| (*Lactobacillus fermentum* KCCM 35461) | 0.078 | After 18 hour incubation |
| *Lactobacillus* NM316 | 0.126 | After 9 hour incubation |
|  | 0.168 | After 18 hour incubation |
| *Lactobacillus* PRD202 | 0.150 | After 12 hour incubation |

EXAMPLE 6

The Change of Weight and Amount of Diet Due to Taking *Lactobacillus reuteri* PRD202 and the Change of Metabolic Efficiency Caused Thereby Nine 5 week-old male SD rats (Sprague Dawley rat) were respectively assigned to phosphate buffered saline (PBS) group, *Lactobacillus reuteri* ATCC23272 group and *Lactobacillus* PRD202 group. *Lactobacillus reuteri* ATCC23272 and *Lactobacillus reuteri* PRD202 were administered on each group by $3 \times 10^{11}$ cfu/dose twice a day.

Upon administering the microorganism for 30 days, as illustrated in Table 7 and FIG. 1, the body weight of SD rats began to be slowly changed on $12^{th}$ day and the change thereof had been decreased approximately 6.5% on the last $30^{th}$ day, as compared with the control group, PBS group.

Figure 2:
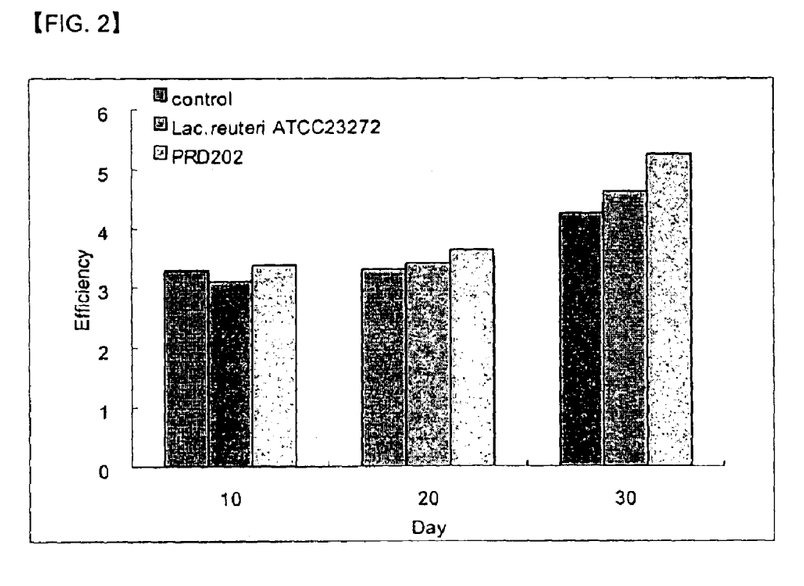
FIG. 2 is the graph illustrating the change of metabolism efficiency of rat that has taken the microorganism of the present invention in the form of live microorganism itself.

In addition, as illustrated in Table 7, *Lactobacillus reuteri* PRD202 group showed the amount of feed intake approximately 8.3% lower than that of PBS group. Upon calculating the metabolic efficiency from the above results, the metabolic efficiency of *Lactobacillus reuteri* PRD202 was 5.6% higher than that of PBS group (FIG. 2) on the 30th day.

Therefore, it was confirmed that the microorganism of the present invention was very effective for treatment or prevention of obesity by converting the absorbed monosaccharides or disaccharides to polysaccharides. In addition, the microorganism of the present invention had an effect on decreasing the amount of feed intake by satiation due to the convert polysaccharides in the body.

TABLE 6

The change of body weight and total feed intake of SD rats after 30 day administration

| | The change of Body weight | | | |
| --- | --- | --- | --- | --- |
| | 0 day | 30 days | The increase of body weight | Total feed intake |
| Control group (PBS group) | 147.1 ± 6.3 | 328.4 ± 6.9 | 181.3 ± 8.9 | 633.5 ± 21.8 |
| *Lactobacillus reuteri* ATCC23272 group | 151.3 ± 3.2 | 320.4 ± 7.1 | 169.9 ± 8.1 | 595.6 ± 17.0 |
| *Lactobacillus* PRD202 group | 150.5 ± 6.0 | 307.3 ± 10.9 | 158.7 ± 12.1 | 585.2 ± 22.9 |

(unit: g)

EXAMPLE 7

The Change of Plasma Cholesterol Level when *Lactobacillus reuteri* PRD202 was Administered The change of plasma cholesterol level was measured in order to confirm whether or not *Lactobacillus reuteri* PRD202 affected the circulatory disease, such as, arteriosclerosis and myocardial infarction besides diabetes mellitus and obesity.

The blood for analysis of cholesterol contents was collected from the tail of each rat. Cholesterol analysis was performed by means of enzyme coloring method, using Cholesterol-V (Shin-Yang Chemical Co.) to measure the absorbance at 505 to 570 nm with standard solution and to calculate the amount of cholesterol contents in blood.

Figure 3:
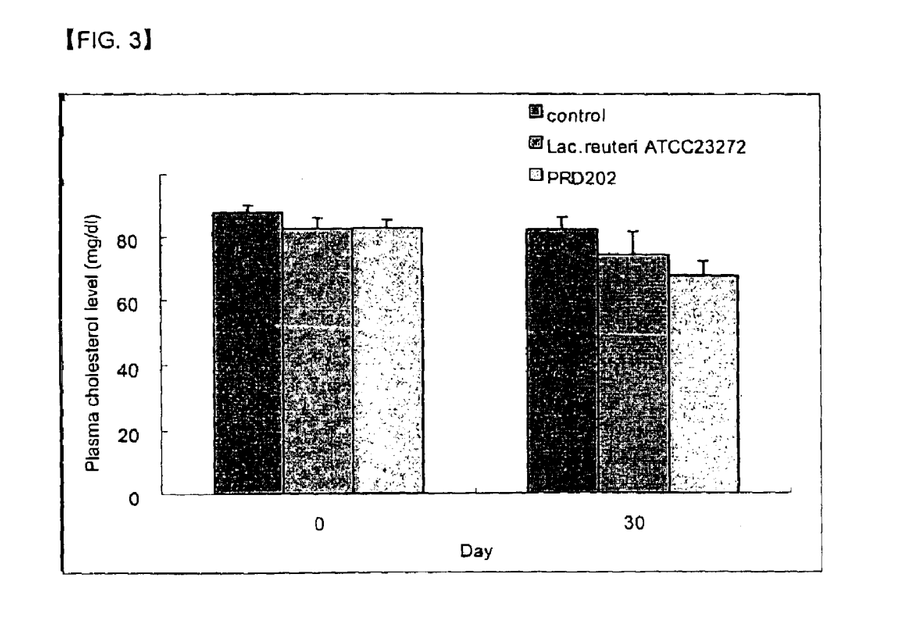
FIG. 3 is the graph illustrating the change of plasma cholesterol level of rat that has taken the microorganism of the present invention in the form of live microorganism itself.

As represented in Table 8 and FIG. 3, plasma cholesterol level of *Lactobacillus reuteri* PRD202 group had been significantly decreased on $30^{th}$ day after administration, as compared with the PBS group (P<0.005).

Therefore, the microorganism of the present invention was also expected to be effective for decreasing circulatory disease (for example, arteriosclerosis, myocardial infarction).

TABLE 7

The change of plasma cholesterol level of SD rats after 30 day administration

| | 0 day | 30 days |
| --- | --- | --- |
| Control group (PBS group) | 87.99 ± 2.11 | 82.46 ± 3.94 |
| *Lactobacillus reuteri* ATCC23272 | 82.81 ± 3.50 | 74.38 ± 7.36 |
| *Lactobacillus* PRD202 group | 82.98 ± 2.64 | 68.01 ± 4.47* |

*P < 0.005 upon comparing the plasma cholesterol level between control group and PRD202 group on $30^{th}$ day
unit: mg/dl

EXAMPLE 8

The Change of Plasma Glucose Level Upon Feeding *Lactobacillus* PRD202

The plasma glucose level of rats was measured in order to confirm whether or not the microorganism of the present invention caused hypoglycemia due to the glucose absorption by the microorganism.

Blood was collected from the tail of each rat by using capillaries containing anticoagulant and then plasma was isolated from the blood.

Figure 4:
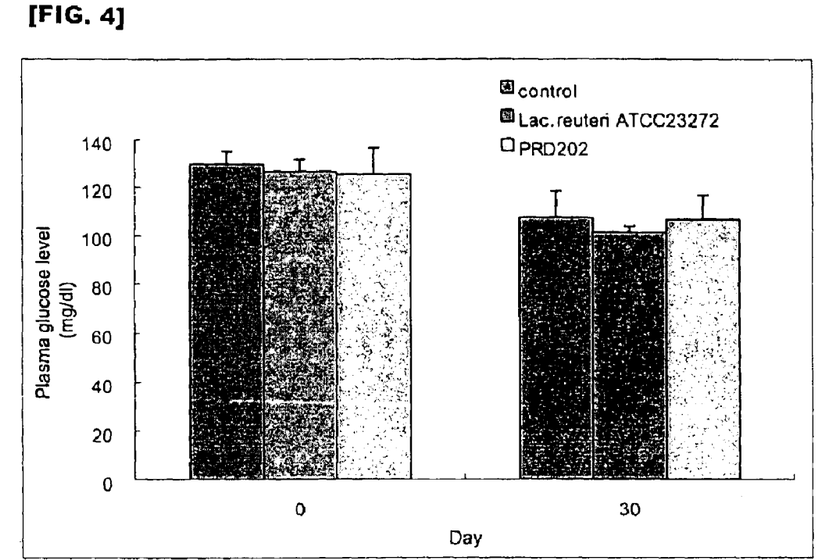
FIG. 4 is the graph illustrating the change of plasma glucose level of rat that has taken the microorganism of the present invention in the form of live microorganism itself.

The plasma glucose level was measured by absorbance at 505 nm, using the Trinder kit (Cat. 325–500, Sigma, USA), which employs enzyme-coloring method. The absorbance of each serum was compared with that of standard solution to calculate plasma glucose level of each serum. The statistical error of the results was indicated by average± standard deviation per experimental group. The plasma glucose levels thus obtained were represented in FIG. 4. As illustrated in FIG. 4, the blood glucose level of rats belonging to PRD202 group was similar to that of normal rats. Therefore, it was learned that the microorganism of the present invention did not cause hypoglycemia (Table 9).

TABLE 8

The change of plasma glucose level of SD rats after 30 day administration

|  | 0 day | 30 days |
| --- | --- | --- |
| Control group (PBS group) | 129.8 ± 5.5 | 107.8 ± 10.7 |
| Lactobacillus reuteri ATCC23272 group | 126.6 ± 5.2 | 101.7 ± 2.5 |
| Lactobacillus PRD202 group | 125.3 ± 11.5 | 106.9 ± 10.1 |

EXAMPLE 9

The Change of Body Weight and Amount of Feed Intake Due to Taking NM316 and the Change of Metabolic Efficiency Caused Thereby Ten 5 week-old male SD rats (Sprague Dawley rat) were respectively assigned to phosphate buffered saline (PBS) group, *Lactobacillus reuteri* ATCC23272 group and *Lactobacillus* NM316 group. *Lactobacillus reuteri* ATCC23272 and *Lactobacillus* NM316 were orally administered on each group by $3\times10^{11}$cfu/dose twice a day.

Figure 7:
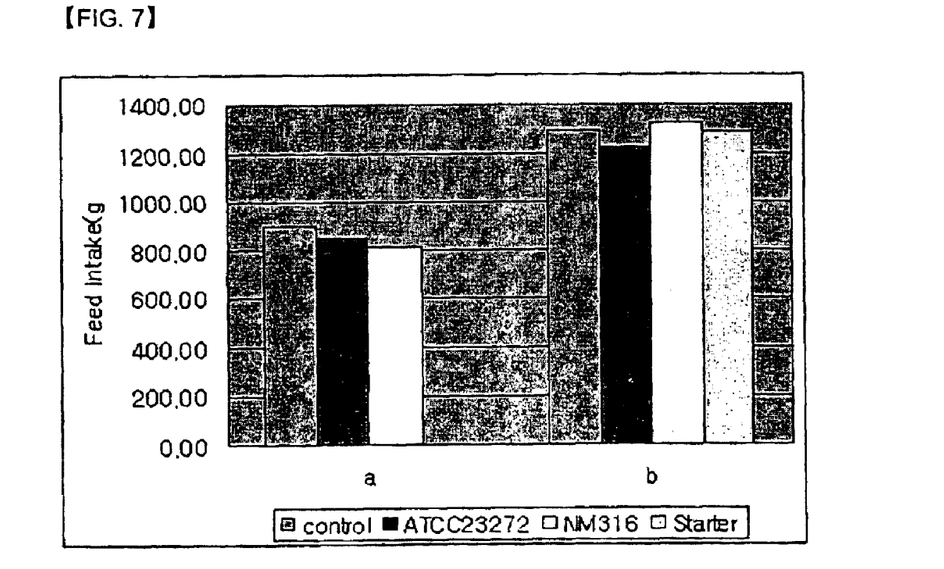
FIG. 7 is the graph illustrating the change of the amount of feed intake of rat that has taken the microorganism of the present invention: a indicates the group wherein the microorganism was administered in the form of live microorganism itself and b indicates the group wherein the microorganism was administered in the form of yogurt.

FIG. 7a represents the change of the amount of feed intake when the microorganism of the present invention was administered in the form of live microorganism itself: The weight of rats and the amount of feed intake in the above figure were expressed as the average calculated from values which measured in 10 rats.

Figure 5:
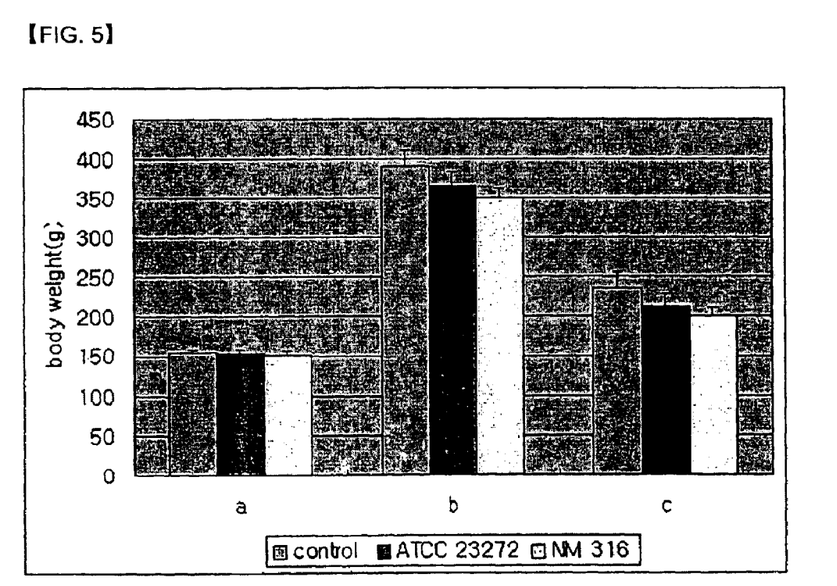
FIG. 5 is the graph illustrating the change of the body weight of rat that has taken the microorganism of the present invention in the form of live microorganism itself: a indicates initial body weight (g), b indicates the body weight (g) after the 40 day administration and c indicates the increase of body weight (g) after the 40 day administration.

As illustrated in FIG. 5 and Table 10, upon administering the microorganism for 40 days, the weight of SD rats began to be slowly changed on $12^{th}$ day and the change thereof had been decreased approximately 10.3% on the last $40^{th}$ day, as compared with the control group, PBS group.

TABLE 9

The weight change of SD rats after 40 day administration

|  | 0 day | 40 days | The increase of body weight |
| --- | --- | --- | --- |
| Control group (PBS group) | 154.09 ± 4.25 | 390.27 ± 19.63 | 236.19 ± 19.19 |
| Lactobacillus reuteri ATCC23272 group | 153.41 ± 4.22 | 365.50 ± 17.09 | 212.09 ± 16.31 |
| Lactobacillus fermentum NM316 group | 151.93 ± 4.60 | 350.03 ± 11.86 | 198.1 ± 12.46 |

In addition, the change of the efficiency of feed intake was measured after *Lactobacillus* NM316 was administered to rats for 40 days.

Figure 8:
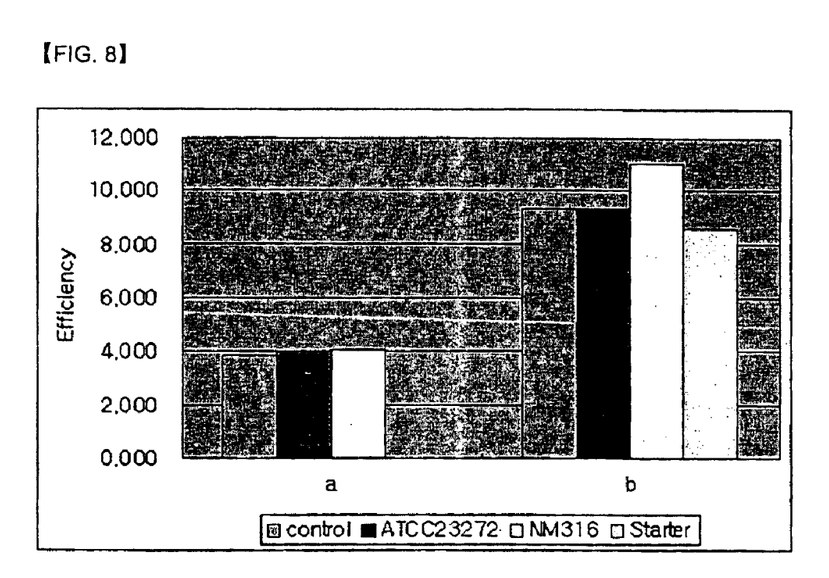
FIG. 8 is the graph illustrating the change of metabolism efficiency of rat that has taken the microorganism of the present invention: a indicates the group wherein the microorganism was administered in the form of live microorganism itself and b indicates the group wherein the microorganism was administered in the form of yogurt.

Total amount of feed intake of rats which had taken the microorganism of the present invention in the form of live microorganism itself, was approximately 10.7% lower than that of the other groups (FIG. 7a). The degree of change of total weight of rats during administration of the microorganism was also approximately 16.1% lower than that of the other groups (FIG. 5). However, the efficiency of feed intake of NM316 group was approximately 6.4% higher than that of PBS group (FIG. 8a).

Consequently, upon compared with PBS group, it was learned that *Lactobacillus fermentum* NM316 could effectively decrease the increase of body weight of rats although the amount of feed intake of the rats had been increased.

EXAMPLE 10

The Change of Weight and Amount of Feed Intake *Lactobacillus fermentum* NM316 in the Form of Yogurt and the Change of Metabolic Efficiency Caused Thereby Ten 5 week-old male SD rats (Sprague Dawley rat) were respectively assigned to five (5) groups. Phosphate buffered saline (PBS), yogurt prepared by using only general starter strains, yogurt containing *Lactobacillus reuteri* ATCC23272 and yogurt containing *Lactobacillus* NM316 were respectively administered to each group.

$7\times10^6$ of the mixture of *Streptococcus thermophillus* and *Lactobacillus bulgaricus* (5:2) was inoculated so as to prepare the basic starter yogurt of the remaining yogurt groups except the PBS group. The live microorganism number of the basic starter yogurt was total $1\times10^8$.

Figure 6:
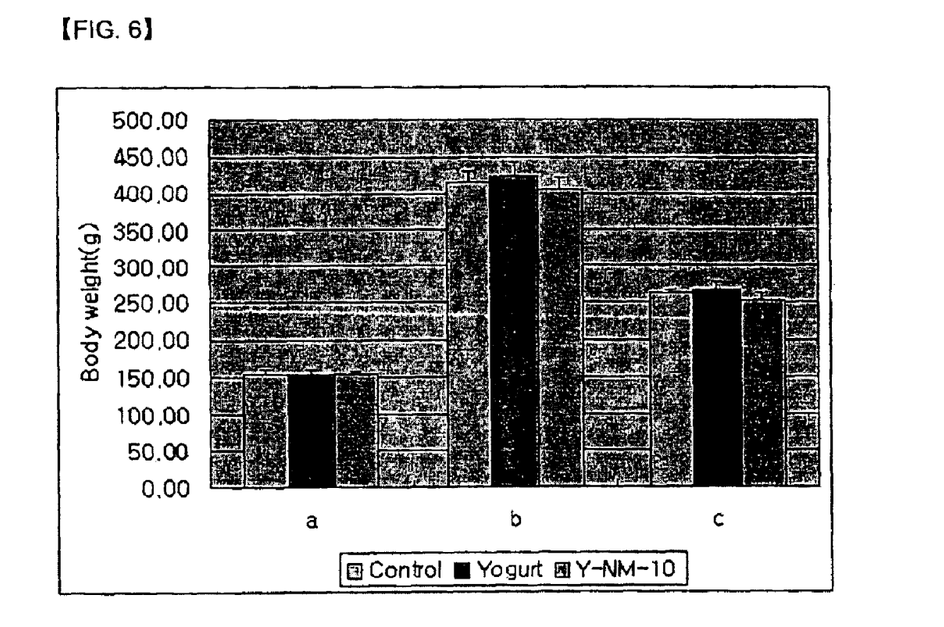
FIG. 6 is the graph illustrating the change of the body weight of rat that has taken the microorganism of the present invention in the form of yogurt: a indicates initial body weight (g), b indicates the body weight (g) after the 60 day administration and c indicates the increase of body weight (g) after the 60 day administration.

*Lactobacillus reuteri* ATCC23272 and *Lactobacillus* NM316 were separately cultured and $4\times10^{10}$cfu thereof were respectively added to the above yogurt. The yogurts thus obtained were orally administered twice a day. As illustrated in FIG. 6 and FIG. 7b, the weight and the amount of feed intake were measured. The measured values were expressed as the average of ten (10) rats.

Upon administering the yogurt for 60 days, the weight of SD rats began to be slowly changed on $44^{th}$ day and the change thereof had been decreased approximately 2.6% on the last $60^{th}$ day, as compared with the control group, PBS group.

Upon comparing the change of the amount of feed intake after administering the yogurt for 60 days, *Lactobacillus fermentum* NM316 group had taken approximately 4.6% more feed than the basic starter yogurt group.

Based on the above, the efficiency of feed intake of NM316 group was approximately 5.2% higher than that of PBS group (FIG. 8b).

Consequently, as learned from the group where the live organism itself was administered, it was learned that *Lactobacillus fermentum* NM316 could effectively decrease the increase of body weight of rats although the amount of feed intake of the rats had been increased.

TABLE 10

The weight change of SD rats after administering the yogurt for 60 days

|  | 0 day | 60 days | The increase of body weight |
| --- | --- | --- | --- |
| Control group (PBS group) | 153.65 ± 6.11 | 413.47 ± 14.02 | 259.83 ± 16.44 |
| The basic starter yogurt | 154.19 ± 6.61 | 420.3 ± 19.33 | 266.11 ± 17.15 |
| Yogurt + Lactobacillus NM316 | 154.7 ± 7.27 | 409.17 ± 19.48 | 254.47 ± 15.22 |

EXAMPLE 11
The Change of Plasma Cholesterol Level when *Lactobacillus fermentum* NM316 was Administered After administration of *Lactobacillus fermentum* NM316 of the present invention, the change of plasma cholesterol level was analyzed in order to confirm whether or not the microorganisms affected the circulatory disease, such as, arteriosclerosis and myocardial infarction besides diabetes mellitus and obesity.

Cholesterol analysis was performed by means of the same method as in Example 8.

Figure 9:
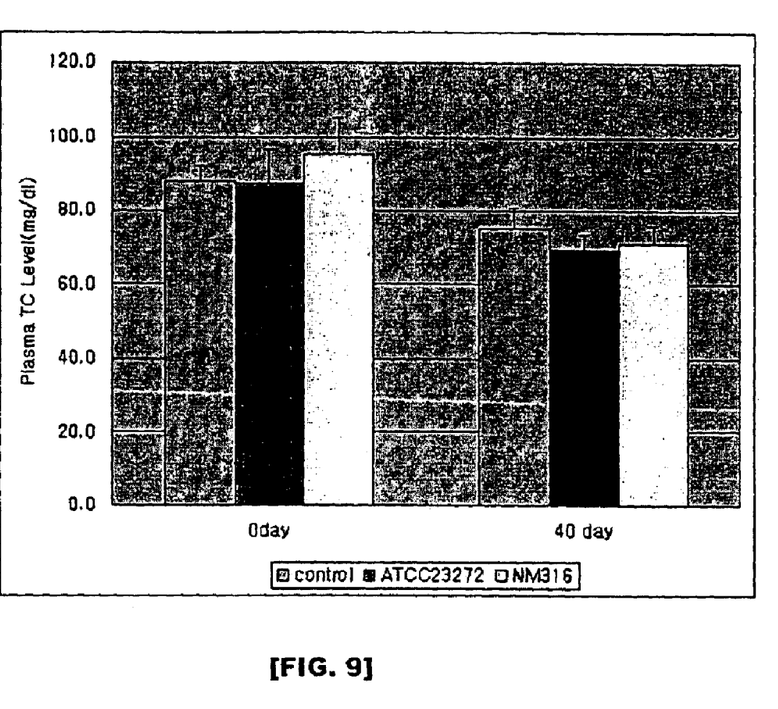
FIG. 9 is the graph illustrating the change of plasma cholesterol level of rat that has taken the microorganism of the present invention in the form of yogurt.

As represented in FIG. 9 and Table 12, plasma cholesterol level began to decrease on $40^{th}$ day, as compared with the PBS group. Therefore, the microorganism of the present invention was expected to decrease circulatory diseases (for example, arteriosclerosis, myocardial infarction).

TABLE 11

The change of plasma cholesterol level of SD rats after 40 day administration in the form of live organism itself

|  | 0 day | 40 days |
|---|---|---|
| Control group (PBS group) | 87.86 ± 4.25 | 75.18 ± 5.67 |
| *Lactobacillus reuteri* ATCC23272 group | 87.58 ± 8.75 | 69.23 ± 4.36 |
| *Lactobacillus* NM316 group | 95.37 ± 9.87 | 70.94 ± 5.11 |

While the present invention has been particularly shown and described with reference to particular examples thereof, it will be understood by those skilled in the art that various changes in form and details may be conceived therefrom without departing from the spirit and scope of the present invention as defined by the appended claims.

The Industrial Applicability of the Present Invention

The microorganisms for the present invention have excellent viability and produce polysaccharides efficiently in the intestines and convert mono or disaccharides such as glucose and fructose into polymeric polysaccharides so as to reduce the amount of monosaccharides or disaccharides that can be absorbed into the intestine. As a result, the microorganisms of the present invention are effective for preventing or treating obesity or diabetes mellitus.

In addition, the microorganisms of the present invention have no harm caused by beta-glucuronidase and are effective for weight control, control of the intestine function and the inhibition of cholesterol absorption.

What is claimed is:

1. A biological pure *Lactobacillus reuteri* PRD202 (KCTC-10301BP) which produces polysaccharides.

2. A biological pure *Lactobacillus fermentum* NM316 (KCTC-10458BP) wich produces polysaccharides.

3. A pharmaceutical composition for preventing or treating obesity or diabetes mellitus comprising an pharmaceutically effective amount of *Lactobacillus reuteri* PRD202 (KCTC-10301BP) which produces polysaccharides and a carrier.

4. The pharmaceutical composition for preventing or treating obesity or diabetes mellitus according to claim 3, wherein the pharmaceutical composition is coated with enteric coating materials.

5. A food composition comprising a food and *Lactobacillus reuteri* PRD202 (KCTC-10301BP) which produces polysaccharides as an active principle.

6. The food composition according to claim 5, wherein the food composition has an effect on the decrease of body weight.

7. A pharmaceutical composition for preventing or treating obesity or diabetes mellitus comprising an pharmaceutically effective amount of *Lactobacillus fermentum* NM316 (KCTC-10458BP) which produces polysaccharides and a carrier.

8. The pharmaceutical composition for preventing or treating obesity or diabetes mellitus according to claim 7, wherein the pharmaceutical composition is coated with enteric coating materials.

9. A food composition a food and *Lactobacillus fermentum* NM316 (KCTG-10458BP) which produces polysaccharides as a active principle.

10. The food composition according to claim 9, wherein the food composition has an effect on the decrease of body weight.

* * * * *

UNITED STATES PATENT AND TRADEMARK OFFICE
CERTIFICATE OF CORRECTION

PATENT NO. : 6,942,857 B2  Page 1 of 1
DATED : September 13, 2005
INVENTOR(S) : Song et al.

It is certified that error appears in the above-identified patent and that said Letters Patent is hereby corrected as shown below:

<u>Column 18,</u>
Lines 7 and 9, please delete "biological" and replace with -- biologically --.

Signed and Sealed this

First Day of November, 2005

JON W. DUDAS
*Director of the United States Patent and Trademark Office*